United States Patent
Song et al.

(10) Patent No.: US 10,173,956 B1
(45) Date of Patent: Jan. 8, 2019

(54) PROCESS FOR CONTINUOUSLY RECOVERING (METH)ACRYLIC ACID AND APPARATUS FOR THE PROCESS

(71) Applicant: LG CHEM, LTD., Seoul (KR)

(72) Inventors: Jong Hun Song, Daejeon (KR); Se Won Baek, Daejeon (KR); Sul Hee Yoo, Daejeon (KR); Yoon Jae Min, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/021,861

(22) Filed: Jun. 28, 2018

Related U.S. Application Data (62) Division of application No. 14/914,233, filed as application No. PCT/KR2014/007944 on Aug. 26, 2014, now Pat. No. 10,035,751.

(30) Foreign Application Priority Data

Aug. 30, 2013 (KR) .................... 10-2013-0104119
Aug. 25, 2014 (KR) .................... 10-2014-0110528

(51) Int. Cl.
| | | |
|---|---|---|
| B01D 11/04 | (2006.01) | |
| B01D 3/00 | (2006.01) | |
| C07C 51/44 | (2006.01) | |
| C07C 51/48 | (2006.01) | |
| B01D 3/14 | (2006.01) | |
| B01L 3/00 | (2006.01) | |
| C07C 51/43 | (2006.01) | |
| C07C 51/47 | (2006.01) | |

(52) U.S. Cl.
CPC .............. *C07C 51/44* (2013.01); *B01D 3/143* (2013.01); *B01D 11/04* (2013.01); *B01L 3/00* (2013.01); *C07C 51/43* (2013.01); *C07C 51/47* (2013.01); *C07C 51/48* (2013.01); *Y02P 20/57* (2015.11)

(58) Field of Classification Search
CPC . B01D 53/265; B01D 53/002; C10L 2290/06; C10L 2290/08; C10L 3/106
See application file for complete search history.

(56) References Cited

U.S. PATENT DOCUMENTS

| | | |
|---|---|---|
| 5,554,329 A | 9/1996 | Monkelbaan et al. |
| 5,618,473 A | 4/1997 | Sauter et al. |
| 6,755,943 B1 | 6/2004 | Mizutani et al. |
| 7,129,387 B2 | 10/2006 | Reyneke et al. |
| 7,306,204 B2 | 12/2007 | Thiel et al. |
| 7,326,323 B2 * | 2/2008 | Mason ................... B01D 3/166 203/1 |

(Continued)

FOREIGN PATENT DOCUMENTS

| | | |
|---|---|---|
| JP | 2000507878 A | 6/2000 |
| JP | 2005509512 A | 4/2005 |

(Continued)

*Primary Examiner* — Cabrena Holecek
(74) *Attorney, Agent, or Firm* — Dentons US LLP (57) ABSTRACT

This disclosure relates to a method for continuous recovery of (meth)acrylic acid and an apparatus used for the recovery method. The method of continuous recovery of (meth) acrylic acid according to the present invention may minimize loss of (meth)acrylic acid particularly in the distillation process, and yet enables stable operation of the distillation process and energy reduction.

4 Claims, 3 Drawing Sheets

(56) References Cited

U.S. PATENT DOCUMENTS

| | | | | |
|---|---|---|---|---|
| 7,723,541 B2 * | 5/2010 | DeCourcy | ............... | C07C 51/44 562/598 |
| 2003/0092937 A1 * | 5/2003 | Wagner | .................. | C07C 51/44 562/600 |
| 2006/0000703 A1 | 1/2006 | Mason | .................. | B01D 3/166 203/99 |
| 2009/0124825 A1 | 5/2009 | Tang et al. | | |
| 2015/0203431 A1 | 7/2015 | Baek et al. | | |

FOREIGN PATENT DOCUMENTS

| | | | |
|---|---|---|---|
| JP | 2006520784 | A | 9/2006 |
| JP | 2009242285 | A | 10/2009 |
| JP | 2013520557 | A | 6/2013 |
| KR | 100349602 | B1 | 3/1999 |
| KR | 1020010006653 | A | 1/2001 |
| KR | 1020040050044 | A | 6/2004 |
| KR | 1020080080049 | A | 9/2008 |
| KR | 1020090041355 | A | 4/2009 |
| KR | 1020090108099 | A | 10/2009 |
| KR | 101143475 | B1 | 4/2012 |

* cited by examiner

PROCESS FOR CONTINUOUSLY RECOVERING (METH)ACRYLIC ACID AND APPARATUS FOR THE PROCESS

This application is a Divisional Application of U.S. application Ser. No. 14/914,233, filed on Feb. 24, 2016, which is a 35 USC § 371 National Stage entry of International Application No. PCT/KR2014/007944, filed on Aug. 26, 2014, and claims priority to, and the benefit of, Korean Patent Application No. 10-2014-0110528, filed on Aug. 25, 2014, and Korean Patent Application No. 10-2013-0104119, filed on Aug. 30, 2013, all of which are hereby incorporated by reference in their entirety as if fully set forth herein.

TECHNICAL FIELD

The present invention relates to a method of continuous recovery of (meth)acrylic acid and an apparatus for the method.

BACKGROUND OF ART (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a reaction product mixed gas including (meth)acrylic acid, non-reacted propane or propylene, (meth)acrolein, an inert gas, carbon dioxide, water vapor, and various organic by-products (acetic acid, heavies, and the like) is obtained in the back end of the reactor.

The (meth)acrylic acid-containing mixed gas contacts an absorption solvent including water in a (meth)acrylic acid absorption tower, and is recovered as a (meth)acrylic acid aqueous solution. Further, (meth)acrylic acid-stripped insoluble gas is recycled for a synthesis reaction of (meth)acrylic acid, and a part thereof is incinerated, converted into harmless gas, and discharged. The (meth)acrylic acid aqueous solution is extracted, distilled, and purified to obtain (meth)acrylic acid.

Figure 1:
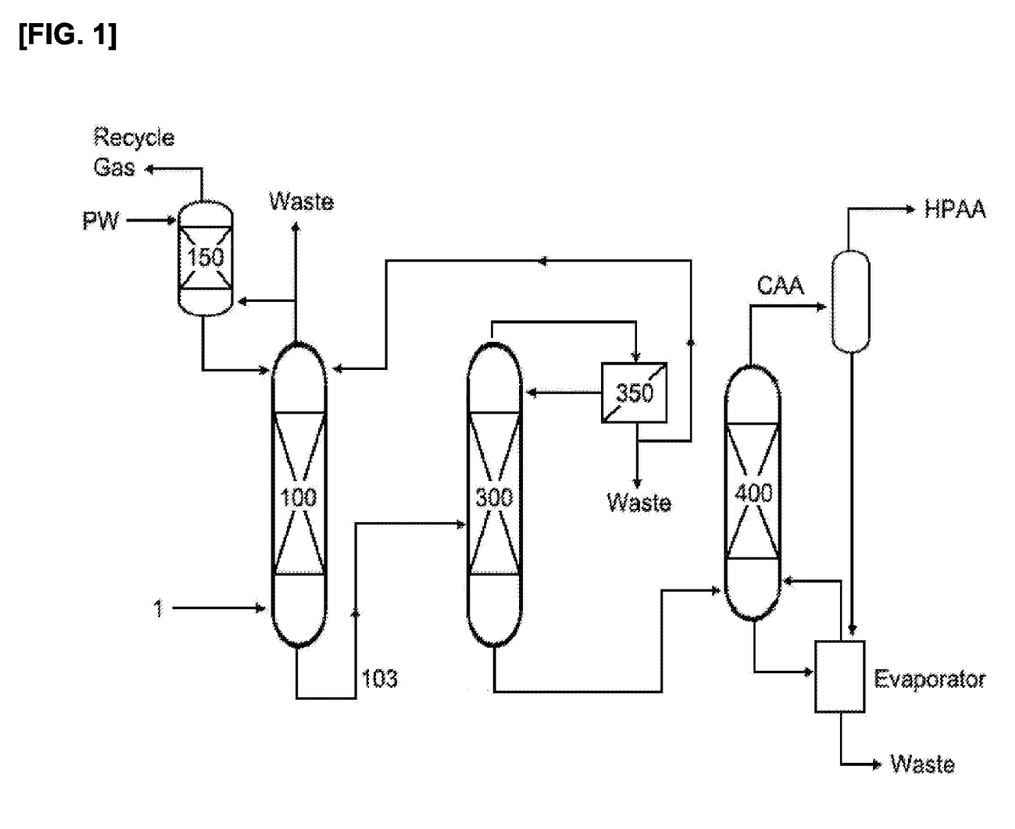
FIG. 1 schematically shows a general method and apparatus for continuous recovery of (meth)acrylic acid.

To improve the recovery efficiency of (meth)acrylic aid, various methods of controlling process conditions or a process sequence and the like are being suggested. Among them, as a method for separating water and acetic acid from the (meth)acrylic acid aqueous solution obtained in the (meth)acrylic acid absorption tower, azeotropic distillation using a hydrophobic solvent in a distillation column (300) as shown in FIG. 1 is known. Further, a method of supplying a (meth)acrylic acid aqueous solution to an extraction column to obtain a (meth)acrylic acid extract solution with reduced water content and a raffinate solution thereof, and distilling the extract solution to obtain (meth)acrylic acid, is known.

However, according to the known methods, there are problems in that loss of (meth)acrylic acid in the distillation process is high, and a temperature profile inside the distillation column appears unstable, thus rendering stable operation of the distillation process difficult.

DETAILED DESCRIPTION OF THE INVENTION

Technical Problem

It is an object of the invention to provide a method of continuous recovery of (meth)acrylic acid that may minimize loss of (meth)acrylic acid in a distillation process, and yet enables stable operation of the distillation process and energy reduction.

It is another object of the invention to provide an apparatus that can be used for the method of continuous recovery of (meth)acrylic acid.

Technical Solution

According to the present invention, a method of continuous recovery of (meth)acrylic acid is provided, including:

an absorption process wherein a mixed gas including (meth)acrylic acid, organic by-products, and vapor, which is produced by a synthesis reaction of (meth)acrylic acid, is contacted with an absorption solvent including water to obtain a (meth)acrylic acid aqueous solution;

an extraction process wherein a part of the (meth)acrylic acid aqueous solution obtained through the absorption process is contacted with an extraction solvent in an extraction column to obtain a (meth)acrylic acid extract solution through the upper outlet of the extraction column and obtain a raffinate solution passing through the lower stationary section of the extraction column through the lower outlet; and a distillation process wherein a feed including the remainder of the (meth)acrylic acid aqueous solution obtained through the absorption process and the (meth)acrylic acid extract obtained through the extraction process is distilled to obtain (meth)acrylic acid, wherein the distillation process is conducted in a distillation column having a plurality of stages partitioned by perforated trays, wherein based on a feed point to which the feed is supplied, perforated trays located at a rectifying section have a lower tray open area ratio than perforated trays located at a stripping section.

According to the present invention, the distillation process may be conducted in a distillation column with the ratio of the tray open area ratio of the perforated trays located at the rectifying section based on the tray open area ratio of the perforated trays located at the stripping section being 1:0.6 to 1:0.9.

According to the present invention, the distillation process may be conducted in a distillation column of which perforated trays are dual-flow-type countercurrent trays.

According to the present invention, the feed point may be any one point corresponding to 40 to 60% of total stages from the uppermost stage of the distillation column.

According to the present invention, an apparatus for continuous recovery of (meth)acrylic acid is provided, including:

a (meth)acrylic acid absorption tower (100) equipped with a mixed gas inlet to which mixed gas including (meth)acrylic acid, organic by-products and vapor, which is produced by a synthesis reaction of (meth)acrylic acid, is fed, and a (meth)acrylic acid aqueous solution outlet from which a (meth)acrylic acid aqueous solution obtained by contact of the mixed gas with an absorption solvent including water is discharged;

a (meth)acrylic acid extraction column (200) equipped with a (meth)acrylic acid aqueous solution inlet connected with the aqueous solution outlet of the absorption tower (100) through an aqueous solution transfer line (102), to which a part of the (meth)acrylic acid aqueous solution is fed, an extract outlet from which the (meth)acrylic acid extract obtained by contact of the introduced (meth)acrylic acid aqueous solution with an extraction solvent is discharged, and a raffinate outlet from which the raffinate solution obtained by contact of the (meth)acrylic acid aqueous solution with an extraction solvent is discharged; and a distillation column (300) equipped with a feed point that is connected with the (meth)acrylic acid aqueous solution outlet of the absorption tower (100) through an aqueous solution transfer line (103), and is connected with the extract outlet of the extraction column (200) through an extract transfer line (203), to which a feed containing the remainder of the (meth)acrylic acid aqueous solution and the extract solution is supplied, and a (meth)acrylic acid outlet from which (meth)acrylic acid obtained by distillation of the introduced feed is discharged, wherein the distillation column has a plurality of stages partitioned by perforated trays, wherein based on the feed point, perforated trays located at a rectifying section have a lower tray open area ratio than perforated trays located at a stripping section.

Advantageous Effects

The method of continuous recovery of (meth)acrylic acid according to the present invention may minimize loss of (meth)acrylic acid particularly in the distillation process, and yet enables stable operation of the distillation process and energy reduction.

REFERENCE NUMERALS

1: (meth)acrylic acid containing mixed gas
100: (meth)acrylic acid absorption tower
102, 103: (meth)acrylic acid aqueous solution transfer line
150: acetic acid absorption tower
200: (meth)acrylic acid extraction column
203: extract transfer line
235: raffinate transfer line
300: distillation column
310: rectifying section
390: stripping section
350: phase separation tank
400: heavies separation tower
CAA: crude (meth)acrylic acid
HPAA: high purity (meth)acrylic acid

DETAILED DESCRIPTION OF THE EMBODIMENTS

Hereinafter, a method of continuous recovery of (meth)acrylic acid and a recovery apparatus according to the embodiments of the invention will be explained.

First, the technical terms used herein are only to mention specific embodiments, and are not intended to limit the invention, and singular forms used herein include plural forms, unless they have clearly opposite meanings. Further, the meaning of 'comprising' as used herein embodies a specific property, area, integer, step, operation, element, or component, and it does not exclude the addition of other specific properties, areas, integers, steps, operations, elements, or components.

Unless otherwise described, terms used herein are defined as follows.

The term '(meth)acrylic acid' generally refers to acrylic acid, methacrylic acid, or a mixture thereof.

Further, the term '(meth)acrylic acid-containing mixed gas' generally refers to a mixed gas that may be produced when (meth)acrylic acid is prepared by gas phase oxidation. As a non-limiting example, the (meth)acrylic acid-containing mixed gas may be obtained by gas phase oxidation of at least one compound selected from the group consisting of propane, propylene, butane, i-butylene, t-butylene, and (meth)acrolein ('raw material compound') in the presence of a catalyst, wherein the (meth)acrylic acid-containing mixed gas may include (meth)acrylic acid, non-reacted raw material compounds, (meth)acrolein, an inert gas, carbon monoxide, carbon dioxide, water vapor, and various organic by-products (acetic acid, heavies, and the like), and the like. Herein, poorly water-soluble floating material formed by the organic by-products is referred to as 'scum'.

The term '(meth)acrylic acid aqueous solution' refers to an aqueous solution containing (meth)acrylic acid, and for example, it may be obtained by contacting the (meth)acrylic acid-containing mixed gas with an absorption solvent containing water.

The term 'rectifying section' of the distillation column refers to an area above a feed point (for example, a point to which a feed containing a (meth)acrylic acid aqueous solution and a (meth)acrylic acid extract solution is fed) of the distillation column, and it means the area in which among the components included in the feed, the concentration of more volatile components increases in the distillation process.

Further, the term 'stripping section' of the distillation column refers to an area below a feed point of the distillation column, and it means the area in which, among the components included in the feed, the concentration of more volatile components decreases in the distillation process.

Figure 3:
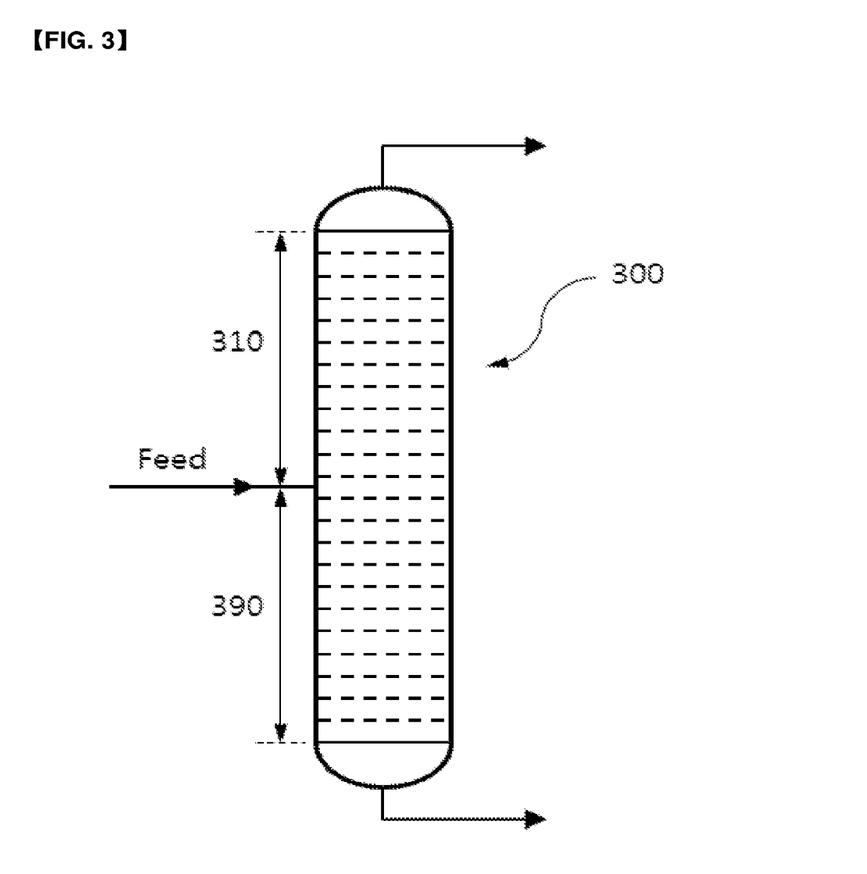
FIG. 3 schematically shows the method and apparatus for continuous recovery of (meth)acrylic acid according to one embodiment of the invention.

For example, in the distillation column (300) of FIG. 3, the rectifying section (310) is the area from the feed point to the uppermost part of the distillation column, and the stripping section (390) is the area from the feed point to the lowermost part of the distillation column. Further, a stage equipped with a feed point in the distillation column is referred to as a 'feed stage'.

Hereinafter, referring to the attached drawings, specific embodiments of the invention will be explained in detail so that one of ordinary knowledge in the art may easily practice it. However, the present invention may be embodied in various forms, and is not limited to the examples.

According to the study results of the inventors, it was confirmed that there is a significant difference between hydraulic parameters of the upper part and the lower part of a feed point of a distillation column. Specifically, it was shown that the liquid level, Flood %, fourth height, and the like at the upper area of the feed point (rectifying section) are significantly lower than those at the lower area of the feed point (stripping section). It was also confirmed that due to the difference, the amount of (meth)acrylic acid loss to the upper part of the distillation column increases, the amount of solvents used for distillation increases, and it is difficult to maintain the temperature inside the distillation column constant, thus rendering stable operation of the distillation process.

Thus, during repeated studies for ameliorating the above problems, the inventors confirmed that if a distillation process is conducted using a distillation column wherein perforated trays located at the rectifying section have a lower tray open area ratio than perforated trays located at the stripping section, loss of (meth)acrylic acid in the distillation process may be minimized, and yet the distillation process may be stably operated and energy consumption may be reduced.

I. A Method of Continuous Recovery of (Meth)Acrylic Acid

According to one embodiment of the invention, a method of continuous recovery of (meth)acrylic acid is provided, including:

an absorption process wherein a mixed gas including (meth)acrylic acid, organic by-products, and vapor, which is produced by a synthesis reaction of (meth)acrylic acid, is contacted with an absorption solvent including water to obtain a (meth)acrylic acid aqueous solution;

an extraction process wherein a part of the (meth)acrylic acid aqueous solution obtained through the absorption process is contacted with an extraction solvent in an extraction column to obtain a (meth)acrylic acid extract solution through the upper outlet of the extraction column and obtain a raffinate solution passing through the lower stationary section of the extraction column through the lower outlet; and a distillation process wherein a feed including the remainder of the (meth)acrylic acid aqueous solution obtained through the absorption process and the (meth)acrylic acid extract obtained through the extraction process is distilled to obtain (meth)acrylic acid, wherein the distillation process is conducted in a distillation column having a plurality of stages partitioned by perforated trays, wherein based on a feed point to which the feed is supplied, perforated trays located at a rectifying section have a lower tray open area ratio than perforated trays located at a stripping section.

The method of continuous recovery of (meth)acrylic acid according to one embodiment of the invention aims at minimizing loss of (meth)acrylic acid through stable operation of the distillation process, and improving energy efficiency and productivity.

Figure 2:
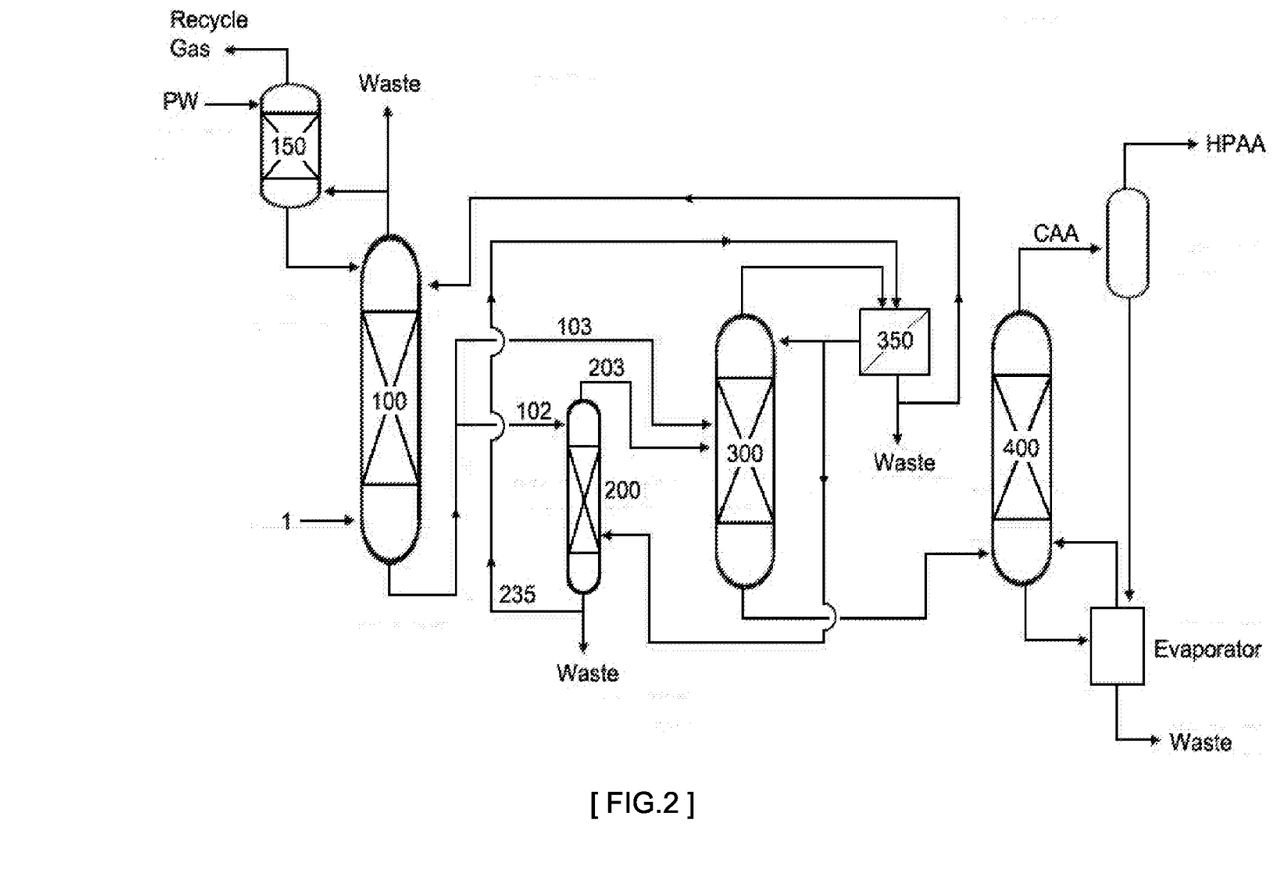
FIG. 2 schematically shows the method and apparatus for continuous recovery of (meth)acrylic acid according to one embodiment of the invention.

Basically, the method of continuous recovery of (meth) acrylic acid according to the present invention includes an absorption process for obtaining a (meth)acrylic acid aqueous solution, an extraction process of the (meth)acrylic acid aqueous solution, and a distillation process of the (meth) acrylic acid aqueous solution and the extract solution, as shown in FIG. 2. Further, in the distillation process, a distillation column having the structure shown in FIG. 3 is used.

Hereinafter, referring to FIG. 2 and FIG. 3, each process that can be included in the embodiment of the invention will be explained in detail.

(Absorption Process)

An absorption process is a process for obtaining a (meth) acrylic acid aqueous solution, and it may be conducted by contacting a (meth)acrylic acid-containing mixed gas obtained through the synthesis reaction of (meth)acrylic acid with an absorption solvent including water.

As a non-limiting example, the synthesis reaction of (meth)acrylic acid may be conducted by the oxidation reaction of at least one compound selected from the group consisting of propane, propylene, butane, isobutylene, and (meth)acrolein in the presence of a gas phase catalyst. Herein, the gas phase oxidation reaction may be progressed using a gas phase oxidation reactor of a common structure and under common reaction conditions. As the catalyst for the gas phase oxidation reaction, common catalysts may be used, and for example, catalysts suggested in Korean Registered Patent No. 0349602 and No. 037818, and the like may be used. In the (meth)acrylic acid-containing mixed gas produced by the gas phase oxidation reaction, in addition to the desired product (meth)acrylic acid, non-reacted raw material compounds, intermediate (meth)acrolein, an inert gas, carbon dioxide, vapor, and various organic by-products (acetic acid, light ends, heavies, and the like) may be included.

Referring to FIG. 2, the (meth)acrylic acid aqueous solution may be obtained by feeding a (meth)acrylic acid-containing mixed gas (1) to a (meth)acrylic acid absorption tower (100), to contact it with an absorption solvent including water.

Herein, the kind of the (meth)acrylic acid absorption tower (100) may be determined considering contact efficiency of the mixed gas (1) with the absorption solvent, and the like. As non-limiting examples, the (meth)acrylic acid absorption tower (100) may be a packed tower or a multistage tray tower. Inside the packed tower, a packing such as a Raschig ring, a pall ring, a saddle, gauze, structured packing, and the like may be applied.

Further, considering the efficiency of the absorption process, the mixed gas (1) may be fed to the lower part of the absorption tower (100), and the solvent including water may be fed to the upper part of the absorption tower (100).

The absorption solvent may include water such as tap water, deionized water, and the like, and it may include recycled process water introduced from other processes (for example, an aqueous phase recycled from an extraction process and/or a distillation process). In the absorption solvent, a trace amount of organic by-products introduced from other processes (for example, acetic acid) may be included. However, considering the absorption efficiency of (meth)acrylic acid, it is preferable that organic by-products may be included in the content of 15 wt % or less in the absorption solvent fed to the absorption tower(100) (particularly, in the recycled process water).

According to the embodiment of the invention, the raffinate solution obtained in a (meth)acrylic acid extraction column (200) may be recycled to the absorption tower (100) and used as an absorption solvent. Herein, it may be advantageous in terms of improvement in process efficiency that the raffinate solution is fed to the upper part of the absorption tower (100).

The (meth)acrylic acid absorption tower (100) may be operated at an internal pressure of 1 to 1.5 bar or 1 to 1.3 bar, and at an internal temperature of 50 to 100° C. or 50 to 80° C., considering condensation conditions and moisture content according to saturated water vapor pressure, and the like.

Meanwhile, in the absorption process, a (meth)acrylic acid aqueous solution is discharged to the lower part of the (meth)acrylic acid absorption tower (100), and (meth)acrylic acid-stripped non-condensable gas is discharged to the upper part thereof. Herein, it may be favorable in terms of the efficiency of the total process that 40 wt % or more, or 40 to 90 wt %, or 50 to 90 wt %, or 50 to 80 wt % of (meth)acrylic acid may be included in the (meth)acrylic acid aqueous solution.

The obtained (meth)acrylic acid aqueous solution, as shown in FIG. 2, are divided and fed to the (meth)acrylic acid extraction column (200) and a distillation column (300) through aqueous solution transfer lines (102 and 103). As shown in FIG. 2, if an extraction process is introduced between a (meth)acrylic acid absorption process and a distillation process, and simultaneously a (meth)acrylic acid aqueous solution is divided and fed to the extraction process and the distillation process, the distillation process may be operated under more relaxed operation conditions than the process sequentially passing through the extraction process and distillation process. Through the process, loss of (meth) acrylic acid in the distillation process may be more minimized, total energy consumption may be reduced, and stable process operation is enabled.

Herein, the ratio of the (meth)acrylic acid aqueous solution divided and fed to the extraction column (200) and the distillation column (300) may be determined considering capacity of each column, treatment performance, energy efficiency improvement effect, and the like. According to one embodiment, it may be favorable for manifestation of the above-explained effect that 5 to 70 wt %, or 10 to 60 wt %, or 10 to 50 wt % of the (meth)acrylic acid aqueous solution may be fed to the extraction column (200), and the remainder may be fed to the distillation column (300).

Meanwhile, at least a part of the non-condensable gas discharged to the upper part of the (meth)acrylic acid absorption tower (100) may be fed to a process of recovering organic by-products (particularly, acetic acid) included in the non-condensable gas, and the remainder may be fed to a waste gas incinerator and discarded. Namely, according to one embodiment of the invention, a process of contacting the non-condensable gas with an absorption solvent to recover acetic acid included in the non-condensable gas may be progressed.

The process of contacting the non-condensable gas with an absorption solvent may be conducted in an acetic acid absorption tower (150). As a non-limiting example, an absorption solvent (process water) for absorbing acetic acid may be fed to the upper part of the acetic acid absorption tower (150), and an aqueous solution containing acetic acid may be discharged to the lower part of the acetic acid absorption tower (150). Further, the acetic acid-containing aqueous solution may be fed to the upper part of the (meth)acrylic acid absorption tower (100) and used as an absorption solvent, and acetic acid-stripped non-condensable gas may be recycled to the synthesis process of (meth) acrylic acid and reused.

For effective absorption of acetic acid, the acetic acid absorption tower (150) may be operated at an internal pressure of 1 to 1.5 bar or 1 to 1.3 bar, and at an internal temperature of 50 to 100° C. or 50 to 80° C. In addition, specific operation conditions of the acetic acid absorption tower (150) may follow the disclosure of Korean Laid-Open Patent Publication No. 2009-0041355.

(Extraction Process)

An extraction process wherein a (meth)acrylic acid aqueous solution is contacted with an extraction solvent in an extraction column to obtain a (meth)acrylic acid extract solution and a raffinate solution is conducted. Herein, the (meth)acrylic acid aqueous solution may be prepared by the above-explained absorption process.

The extraction process may be conducted in a (meth) acrylic acid extraction column (200). The (meth)acrylic acid aqueous solution fed to the extraction column (200) contacts an extraction solvent, and is discharged as an extract solution in which a significant amount of (meth)acrylic acid is dissolved and a raffinate solution that is deprived of a significant amount of (meth)acrylic acid, respectively. Herein, the extraction solution that is in a relatively light phase is obtained through the upper outlet of the extraction column (200), and the raffinate solution that is in a relatively heavy phase is obtained through the lower outlet of the extraction column. Before the raffinate solution is discharged from the extraction column (200), a certain amount thereof remains stationary at the stationary section of the lower part of the extraction column, and a part thereof is discharged to the lower outlet of the extraction column.

As such, by contacting the (meth)acrylic acid aqueous solution with an extraction solvent in an extraction column (200) (namely, extraction with small energy consumption compared to distillation), most water included in the (meth) acrylic acid aqueous solution may be removed. Thereby, the treatment load of the subsequent distillation process may be lowered, thus improving energy efficiency of the total process. Furthermore, by lowering the treatment load of the distillation process, polymerization of (meth)acrylic acid that may be generated during distillation may be minimized, to secure more improved recovery efficiency of (meth) acrylic acid.

Further, in the extraction process, the raffinate solution may be fed to a phase separation tank (350) through a raffinate transfer line (235) and phase separated into an aqueous phase and an organic phase together with the upper discharged solution of the distillation column (300). However, since scum may be included in the raffinate solution, it may be preferable in terms of operation stability that the raffinate solution is filtered to remove scum, and then the filtrate is fed to the phase separation tank (350). Selectively, the raffinate may be recycled to the absorption process and used as a (meth)acrylic acid absorption solvent.

Meanwhile, it is preferable that the extraction solvent fed to the extraction column (200) may have solubility and hydrophobicity to (meth)acrylic acid. Further, considering the kind of solvent and the properties required in the subsequent distillation process, it is preferable that the extraction solvent may have a lower boiling point than (meth)acrylic acid. According to one embodiment of the invention, it is advantageous for process operation that the extraction solvent may be a hydrophobic solvent having a boiling point of 120° C. or less, or 10 to 120° C., or 50 to 120° C.

Specifically, the extraction solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

The feed amount of the extraction solvent may be controlled such that the weight ratio of the (meth)acrylic acid aqueous solution and the extraction solvent fed to the extraction column (200) may be 1:1 to 1:2, or 1:1.0 to 1:1.8, or 1:1.1 to 1:1.5, or 1:1.1 to 1:1.3. Namely, in order to secure appropriate extraction efficiency, it is preferable that the weight ratio of the (meth)acrylic acid aqueous solution and the extraction solvent fed to the extraction column (200) is maintained at 1:1 or more. If the weight ratio exceeds 1:2, although extraction efficiency may be improved, loss of (meth)acrylic acid at a distillation column (300) of the subsequent process may increase, and reflux of an azeotropic solvent for blocking it may excessively increase, which is not preferable.

According to one embodiment of the invention, it is favorable for securing extraction efficiency that the temperature of the (meth)acrylic acid aqueous solution fed to the extraction column (200) may be 10 to 70° C.

As the extraction column (200), common extraction columns of a liquid-liquid contact type may be used without specific limitations. As non-limiting examples, the extraction column (200) may be a Karr-type reciprocating plate column, a rotary-disk contactor, a Scheibel column, a Kuhni column, a spray extraction tower, a packed extraction tower, a pulsed packed column, and the like.

Through the extraction process, a (meth)acrylic acid extract solution is discharged to the upper part of the extraction column (200), and the discharged extract solution is fed to a distillation column (300) through a transfer line (203). A raffinate solution is discharged to the lower part of the extraction column (200), and the discharged raffinate solution may pass through a filtering system (250) as necessary, and then be recycled to the (meth)acrylic acid absorption tower (100).

Herein, in the extract solution, in addition to the desired compound (meth)acrylic acid, an extraction solvent, water, and organic by-products may be included. As non-limiting examples, at a steady state where stable operation is conducted, 30 to 40 wt % of (meth)acrylic acid, 55 to 65 wt % of an extraction solvent, 1 to 5 wt % of water, and the remaining amount of organic by-products may be included in the extract solution. Namely, most water (for example, 85 wt % or more of water included in the aqueous solution) included in the (meth)acrylic acid aqueous solution may be recovered as a raffinate solution through the extraction process. As most water is recovered from the extraction column (200), the distillation load of a distillation column (300) may be reduced to lower energy consumption, and since distillation conditions may be relaxed, polymerization of (meth)acrylic acid may be minimized in the distillation process, thus securing operation stability and improving recovery efficiency of (meth)acrylic acid.

Further, in the raffinate solution discharged through the lower outlet of the extraction column (200), non-extracted (meth)acrylic acid may be included. However, according to the above-explained embodiment of the invention, 5 wt % or less, or 0.5 to 5 wt %, or 1 to 3 wt % of (meth)acrylic acid may be included in the raffinate solution, thus minimizing the loss of (meth)acrylic acid in the absorption process and extraction process.

(Distillation Process)

A distillation process wherein a feed including the (meth) acrylic acid extract solution is distilled to obtain (meth) acrylic acid is conducted.

According to the embodiment, the feed may be a mixture of the (meth)acrylic acid aqueous solution fed from the above explained absorption process and the (meth)acrylic acid extract solution fed from the above-explained extraction process. In this case, the feed may be simultaneously fed to the feed point of a distillation column (300) through a (meth)acrylic acid aqueous solution transfer line (103) and a (meth)acrylic acid extract solution transfer line (203), as shown in FIG. 2.

According to the embodiment of the invention, the distillation process may be conducted in a distillation column (300) having a plurality of stages partitioned by perforated trays, as shown in FIG. 3. Herein, the stage means a location where condensation of vapor moving to the upper part of the distillation column and evaporation of liquid moving to the lower part of the distillation column occur.

Particularly, according to the embodiment of the invention, the distillation process may be conducted in a distillation column (300) wherein, based on a feed point to which a feed including (meth)acrylic acid is supplied, perforated trays located at a rectifying section have a lower tray open area ratio than perforated trays located at a stripping section.

In this regard, according to the study results of the inventors, it was confirmed that the liquid level, Flood %, froth height, and the like at the rectifying section which is the upper area of the feed point are much lower than those at the stripping section which is the lower area of the feed point. Further, it was confirmed that due to the difference, the amount of (meth)acrylic acid that cannot be recovered to the lower part of the distillation column and is lost to the upper part increases, the amount of azeotropic solvents used for distillation increases, and it is difficult to maintain the temperature inside the distillation column constant, thus rendering stable operation of the distillation process difficult.

According to the embodiment of the invention, the above problems may be overcome by conducting a distillation process in a distillation column wherein perforated trays located at the rectifying section (310) have a lower tray open area ratio than perforated trays located at the stripping section (390). Namely, by varying the tray open area ratios of perforated trays of the upper part and the lower part based on the feed point of the distillation column (300), a difference in hydraulic parameters of the upper part and the lower part may be reduced. Through this, loss of (meth)acrylic acid in the distillation process may be minimized, the distillation process may be stably operated, and energy consumption may be reduced. Furthermore, as shown in FIG. 2, by dividing the (meth)acrylic acid aqueous solution obtained through the absorption process and feeding them into the extraction process and distillation process, the distillation process may be conducted under more relaxed operation conditions, which is advantageous for solving the above problems.

Particularly, the effects resulting from controlling tray open area ratio may be more substantial when the perforated trays are dual-flow type countercurrent trays without a downcomer.

In this regard, in the distillation process, the perforated trays of the distillation column (300) may be cross-flow trays or dual-flow countercurrent trays. However, although the cross-flow tray is equipped with a weir and a downcomer and thus may be relatively advantageous for maintaining a liquid level of a constant height, it may be inappropriate for a commercial distillation process due to difficulty in controlling polymer production in the distillation process. Thus, it is advantageous that a dual-flow type countercurrent tray is applied in a commercial distillation process with high feed throughput. However, since the dual-flow type is not equipped with a wier and a downcomer and thus may have difficulty in maintaining a liquid level of a constant height, by controlling the tray open area ratios of the rectifying section (310) and the stripping section (390) according to one embodiment, productivity may be improved.

According to the embodiment of the invention, the distillation process may be preferably conducted in a distillation column (300) with the tray open area ratio of perforated trays located at the rectifying section (310) based on the tray open area ratio of perforated trays located at the stripping section (390) (namely, tray open area ratio of perforated trays located at the stripping section to tray open area ratio of perforated trays located at the rectifying section) being 1:0.6 to 1:0.9, or 1:0.65 to 1:0.9, or 1:0.65 to 1:0.85, or 1:0.65 to 1:0.8.

According to the embodiment of the invention, it is advantageous that the tray open area ratio of perforated trays located at the rectifying section (310) is controlled to 90% or less compared to the tray open area ratio of perforated trays located at the stripping section (390), so as to sufficiently achieve the effects resulting from controlling of tray open area ratio. However, if the tray open area ratio of the rectifying section (310) is excessively low, azeotropic solvents fed to the upper part of the distillation column (300) may not smoothly come down to a feed point, and even if the azeotropic solvents come down to the feed point, froth height of the rectifying section (310) may become too high, thus generating flooding. Thus, it is advantageous that the tray open area ratio of perforated trays located at the rectifying section (310) is controlled to 60% or more compared to the tray open area ratio of perforated trays located at the stripping section (390).

Meanwhile, according to the embodiment of the invention, the feed including (meth)acrylic acid may be a mixture of the (meth)acrylic acid aqueous solution and the (meth)acrylic acid extract solution. In this case, the feed may be fed to a distillation column (300) through a (meth)acrylic acid aqueous solution transfer line (103) and a (meth)acrylic acid extract solution transfer line (203).

Herein, for effective distillation, it is preferable that the feed point may be a central part of the distillation column (300). Namely, the feed point may be any one point corresponding to 40 to 60% of total stages from the uppermost stage of the distillation column (300).

As the feed supplied to the distillation column (300) contacts an azeotropic solvent introduced into the upper part of the distillation column (300) and is heated to an optimum temperature, distillation by evaporation and condensation is achieved. Herein, in order to effectively separate (meth)acrylic acid included in the feed from the remaining components (for example, water, acetic acid, extraction solvents, and the like), the distillation is preferably conducted by azeotropic distillation.

A solvent used for the azeotropic distillation is preferably a hydrophobic azeotropic solvent that may form an azeotrope with water and acetic acid, and may not form an azeotrope with (meth)acrylic acid. The hydrophobic azeotropic solvent preferably has a lower boiling point than (meth)acrylic acid (for example, a boiling point of 120 t or less, or 10 to 120° C., or 50 to 120° C.).

Specifically, the hydrophobic azeotropic solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Particularly, in case the extraction process is introduced as in FIG. 2, considering production efficiency according to a continuous process, it is preferable that the hydrophobic azeotropic solvent is identical to the extraction solvent of the extraction process. As such, if the same kind of solvents are used in the extraction process and the distillation process, at least a part of the solvent that is distilled in the distillation column (300) and recovered through a phase separation tank (350) may be fed to the (meth)acrylic acid extraction column (200) and reused as an extraction solvent.

Through the distillation process, among the feed, components other than (meth)acrylic acid are discharged to the upper part of the distillation column (300) together with the azeotropic solvent, and (meth)acrylic acid is discharged to the lower part of the distillation column (300).

The upper discharged solution of the distillation column (300) may be fed to a phase separation tank (350) and reused after a predetermined treatment. Herein, the phase separation tank (350) is an apparatus for separating immiscible liquids by gravity or centrifugal force and the like, wherein a relatively light liquid (for example, an organic phase) may be recovered from the upper part of the phase separation tank(350) and a relatively heavy liquid (for example, an aqueous phase) may be recovered from the lower part of the phase separation tank(350).

For example, the upper discharged solution of the distillation column (300) may be separated into an organic phase including an azeotropic solvent and an aqueous phase including water in the phase separation tank (350). Further, the raffinate solution and the filtrate obtained through filtering of the raffinate solution in the above-explained extraction process may be fed to the phase separation tank (350) and phase separated together with the upper discharged solution of the distillation column(300). The separated organic phase may be fed to the upper part of the distillation column (300) and used as an azeotropic solvent, and if necessary, at least a part of the organic phase may be fed to the extraction column (200) and used as an extraction solvent.

At least a part of the aqueous phase separated in the phase separation tank (350) may be fed to the (meth)acrylic acid absorption tower (100) and used as an absorption solvent, and a part thereof may be treated as waste water. In the aqueous phase, acetic acid may be partly included, and the concentration of acetic acid included in the aqueous phase may vary according to the kind of azeotropic solvents and a reflux ratio and the like. As non-limiting examples, the concentration of acetic acid included in the aqueous phase may be 1 to 50 wt %, or 2 to 40 wt %, or 3 to 30 wt %.

Meanwhile, while the (meth)acrylic acid aqueous solution passes through the (meth)acrylic acid absorption tower (100), extraction column (200), distillation column (300), and the like, at least a part of (meth)acrylic acid included in the aqueous solution may form dimers or oligomers. To minimize such polymerization of (meth)acrylic acid, common polymerization inhibitors may be added to the distillation column (300).

In the lower discharged solution of the distillation column (300), in addition to (meth)acrylic acid, heavies such as a polymer of (meth)acrylic acid, polymerization inhibitors, and the like may be included. Thus, if necessary, a step of feeding the lower discharged solution of the distillation column (300) to a high boiling point by-products separation tower (400) and separating heavies included in the lower discharged solution may be further conducted. Crude (meth)acrylic acid (CAA) recovered through the process may be passed through an additional crystallization process and obtained as high purity (meth)acrylic acid (HPAA). Herein, the heavies separation process and the crystallization process and the like may be conducted under common conditions, and the process conditions are not specifically limited.

Meanwhile, in the method of continuous recovery of (meth)acrylic acid, each above-explained step may be conducted organically and continuously. In addition to the above-explained steps, processes that can be commonly conducted before or after or simultaneously with each step may be further included.

II. An Apparatus for Continuous Recovery of (Meth)Acrylic Acid

According to another embodiment of the invention, an apparatus for continuous recovery of (meth)acrylic acid is provided, including:

a (meth)acrylic acid absorption tower (100) equipped with a mixed gas inlet to which mixed gas including (meth) acrylic acid, organic by-products, and vapor, which is produced by a synthesis reaction of (meth)acrylic acid, is fed, and a (meth)acrylic acid aqueous solution outlet from which a (meth)acrylic acid aqueous solution obtained by contact of the mixed gas with an absorption solvent including water is discharged;

a (meth)acrylic acid extraction column (200) equipped with a (meth)acrylic acid aqueous solution inlet connected with the aqueous solution outlet of the absorption tower (100) through an aqueous solution transfer line (102), to which a part of the (meth)acrylic acid aqueous solution is fed, an extract outlet from which the (meth)acrylic acid extract obtained by contact of the introduced (meth)acrylic acid aqueous solution with an extraction solvent is discharged, and a raffinate outlet from which the raffinate solution obtained by contact of the (meth)acrylic acid aqueous solution with an extraction solvent is discharged; and a distillation column (300) equipped with feed point that is connected with the (meth)acrylic acid aqueous solution outlet of the absorption tower (100) through an aqueous solution transfer line (103), and is connected with the extract outlet of the extraction column (200) through an extract transfer line (203), to which a feed containing the remainder of the (meth)acrylic acid aqueous solution and the extract solution is supplied, and a (meth)acrylic acid outlet from which (meth)acrylic acid obtained by distillation of the introduced feed is discharged, wherein the distillation column has a plurality of stages partitioned by perforated trays, wherein based on the feed point, perforated trays located at a rectifying section have a lower tray open area ratio than perforated trays located at a stripping section.

The apparatus for continuous recovery of (meth)acrylic acid of the embodiment may be operated according to the above-explained method for continuous recovery of (meth) acrylic acid.

FIG. 3 schematically show the structure of the cross-section of a distillation column used in the apparatus for continuous recovery of (meth)acrylic acid according to one embodiment of the invention.

Specifically, the distillation column (300) has a plurality of stages partitioned by perforated trays. Herein, the stage means a place where condensation of vapor moving to the upper part of the column and evaporation of liquid moving to the lower part of the column occur.

Particularly, according to one embodiment, by varying the tray open area ratios of perforated trays of the upper part and the lower part based on the feed point of the distillation column (300), a difference in hydraulic parameter of the upper part and the lower part may be reduced. Through this, loss of (meth)acrylic acid in the distillation process may be minimized, the distillation process may be stably operated, and energy consumption may be reduced.

The controlling of tray open area ratio may achieve substantial effects when the perforated trays are dual-flow type countercurrent trays without a downcomer, as explained above.

As explained above, it is preferable that the ratio of the tray open area ratio of perforated trays located at the rectifying section (310) based on the tray open area ratio of perforated trays located at the stripping section (390) of the distillation column (300) is controlled to 1:0.6 to 1:0.9, or 1:0.65 to 1:0.9, or 1:0.65 to 1:0.85, or 1:0.65 to 1:0.8.

It is preferable that the feed point is a central part of the distillation column (300) so as to achieve efficient distillation. Namely, the feed point may be any one point corresponding to 40 to 60% of total stages from the uppermost stage of the distillation column (300).

Meanwhile, the (meth)acrylic acid absorption tower (100) may be a packed tower or a multistage tray tower for improving contact efficiency of the (meth)acrylic acid-containing mixed gas (1) with an absorption solvent including water. Inside of the packed tower, packing such as a Raschig ring, a pall ring, a saddle, gauze, structured packing, and the like may be applied.

As the (meth)acrylic acid extraction column (200), common extraction columns of a liquid-liquid contact type may be used without specific limitation. As non-limiting examples, the extraction column may be a Karr-type reciprocating plate column, a rotary-disk contactor), a Scheibel column, a Kuhni column, a spray extraction column, a packed extraction tower, a pulsed packed column, and the like.

In addition, the acetic acid absorption tower (150), (meth) acrylic acid aqueous solution transfer line (102), extract transfer line (203), phase separation tank(350), high boiling point separation tower (400), and the like may have constructions common in the technical field to which the invention pertains.

Hereinafter, preferable examples are presented to aid in understanding of the invention. However, these examples are only to illustrate the invention, and the scope of the invention is not limited thereto.

Comparative Example 1

Using a pilot device for recovery of acrylic acid with the construction of FIG. 1, the following processes were continuously conducted. Further, the mass flow and the composition of each process are shown in the following Table 1.

An acrylic acid aqueous solution (acrylic acid about 68 wt %) was prepared through an acrylic acid absorption process, and the aqueous solution was fed to a distillation column (300) through a transfer line (103).

Meanwhile, as a distillation column (300), a dual flow tray pilot column (inner diameter of 30 mm, total of 28 stages, tray spacing of 100 mm, tray open area ratio of perforated trays of about 23%) was prepared, and the operation pressure was maintained at about 110 torr. A feed including the acrylic acid aqueous solution was introduced into the $14^{th}$ stage from the uppermost stage of the distillation column (300) at a mass flow of about 6.5 g/min. As an azeotropic solvent, toluene reflux flow separated from the phase separation tank (350) was introduced into the $1^{st}$ stage, the uppermost stage of the distillation column (300), at a mass flow of about 11.95 g/min. Heat was supplied through a reboiler at the lower stage of the distillation column (300).

After stable operation was conducted, at a steady state, distillate was discharged through the upper part of the distillation column (300) at a mass flow of about 14.1 g/min, and acrylic acid flow was obtained through the lower part of the distillation column (300) at a mass flow of about 4.45 g/min. Herein, at a steady state, the temperature of the upper part of the distillation column was maintained at about 40° C., and the temperature of the lower part of the distillation column (300) was maintained at about 97° C.

Comparative Example 2

Acrylic acid flow was obtained by the same method as Comparative Example 1, except that based on the $14^{th}$ stage, which is a feed point of the distillation column (300), at the upper part of a rectifying section, perforated trays with an tray open area ratio of about 17% were applied, and at the lower part of a stripping section, perforated trays with an tray open area ratio of about 23% were applied. The mass flow and the composition of each process are shown in the following Table 2.

TABLE 1

|  |  | Acrylic acid aqueous solution | Reflux flow of azeotropic solvent | Upper organic layer flow of distillation column | Upper aqueous layer flow of distillation column | Lower flow of distillation column |
|---|---|---|---|---|---|---|
| Mass flow (g/min) |  | 6.53 | 11.97 | 11.95 | 2.11 | 4.44 |
| Composition (wt %) | Toluene | 0.00 | 99.74 | 99.76 | 0.06 | 0.00 |
|  | Acrylic acid | 68.01 | 0.16 | 0.08 | 0.76 | 99.78 |
|  | Acetic acid | 2.02 | 0.10 | 0.11 | 6.00 | 0.02 |
|  | Water | 29.97 | 0.00 | 0.06 | 93.18 | 0.00 |
|  | Heavies | 0.00 | 0.00 | 0.00 | 0.00 | 0.00 |

TABLE 2

|  |  | Acrylic acid aqueous solution | Reflux flow of azeotropic solvent | Upper organic layer flow of distillation column | Upper aqueous layer flow of distillation column | Lower flow of distillation column |
|---|---|---|---|---|---|---|
| Mass flow (g/min) |  | 6.50 | 11.95 | 12.03 | 2.11 | 4.31 |
| Composition (wt %) | Toluene | 0.00 | 99.74 | 99.77 | 0.06 | 0.00 |
|  | Acrylic acid | 67.93 | 0.16 | 0.06 | 0.55 | 99.78 |
|  | Acetic acid | 2.02 | 0.10 | 0.12 | 6.11 | 0.02 |
|  | Water | 30.05 | 0.00 | 0.06 | 93.28 | 0.00 |
|  | Heavies | 0.00 | 0.00 | 0.00 | 0.00 | 0.20 |

As shown in Table 1, in the case of Comparative Example 1, the concentration of acrylic acid included in the upper organic layer flow of the distillation column was confirmed to be 0.08 wt %, and the concentration of acrylic acid included in the upper aqueous layer flow was confirmed to be 0.76 wt %.

Further, as shown in Table 2, in the case of Comparative Example 2 wherein the tray open area ratio of perforated trays of the rectifying section was adjusted to 17%, the concentration of acrylic acid included in the upper organic layer flow and the concentration of acrylic acid included in the upper aqueous layer flow of the distillation column slightly decreased to 0.06 wt % and 0.55 wt %, respectively, compared to Comparative Example 1, but the decrease in loss was insignificant.

The temperature profile inside the distillation column was relatively stably maintained both in Comparative Example 1 and Comparative Example 2.

Comparative Example 3

Using a pilot device for recovery of acrylic acid with the construction of FIG. 2, the following processes were continuously conducted. The mass flow and the composition of each process are shown in the following Table 3.

An acrylic acid aqueous solution (acrylic acid at about 68 wt %) was prepared through an acrylic acid absorption process, and an acrylic acid extract solution (acrylic acid at about 32 wt %, toluene at about 65 wt %) was prepared through an acrylic acid extraction process. The aqueous solution and the extract solution were respectively fed to a distillation column (300) through each transfer line (103, 203).

Meanwhile, as a distillation column (300), a dual flow tray pilot column (inner diameter of 30 mm, total of 28 stages, tray spacing of 100 mm, tray open area ratio of perforated trays of about 23%) was prepared, and the operation pressure was maintained at about 110 torr.

The prepared acrylic acid aqueous solution was fed to the $14^{th}$ stage of the distillation column (300) at a mass flow of about 6.08 g/min, and the prepared acrylic acid extract solution was fed to the $14^{th}$ stage of the distillation column (300) at a mass flow of about 6.56 g/min.

As an azeotropic solvent, toluene reflux flow separated from the phase separation tank (350) was introduced into the $1^{st}$ stage, the uppermost stage of the distillation column (300), at a mass flow of about 7.68 g/min. Further, heat was supplied through a reboiler at the lower stage of the distillation column (300).

After stable operation was conducted, at a steady state, a distillate was discharged through the upper part of the distillation column (300) at a mass flow of about 14.0 g/min, and acrylic acid flow was obtained through the lower part of the distillation column (300) at a mass flow of about 6.3 g/min. Herein, at a steady state, the temperature of the upper part of the distillation column was maintained at about 40° C., and the temperature of the lower part of the distillation column (300) was maintained at about 97° C.

Example 1

Acrylic acid flow was obtained by the same method as Comparative Example 3, except that based on the $14^{th}$ stage, which is a feed point of the distillation column (300), at the upper part of a rectifying section, perforated trays with an tray open area ratio of about 17% were applied, and at the lower part of a stripping section, perforated trays with an tray open area ratio of about 23% were applied. The mass flow and the composition of each process are shown in the following Table 4.

TABLE 3

|  |  | Acrylic acid aqueous solution | Acrylic acid extract solution | Reflux flow of azeotropic solvent | Upper organic layer flow of distillation column | Upper aqueous layer flow of distillation column | Lower flow of distillation column |
|---|---|---|---|---|---|---|---|
| Mass flow (g/min) |  | 6.08 | 6.56 | 7.68 | 11.87 | 2.12 | 6.33 |
| Composition (wt %) | Toluene | 0.00 | 65.09 | 99.74 | 99.52 | 0.06 | 0.00 |
|  | Acrylic acid | 68.01 | 32.18 | 0.16 | 0.15 | 1.27 | 99.91 |
|  | Acetic acid | 2.02 | 0.85 | 0.10 | 0.20 | 6.87 | 0.03 |
|  | Water | 29.97 | 1.82 | 0.00 | 0.06 | 91.80 | 0.00 |
|  | Heavies | 0.00 | 0.06 | 0.00 | 0.00 | 0.00 | 0.06 |

TABLE 4

|  |  | Acrylic acid aqueous solution | Acrylic acid extract solution | Reflux flow of azeotropic solvent | Upper organic layer flow of distillation column | Upper aqueous layer flow of distillation column | low flow of distillation column |
|---|---|---|---|---|---|---|---|
| Mass flow (g/min) |  | 6.08 | 6.56 | 7.68 | 11.87 | 2.12 | 6.29 |
| Composition (wt %) | Toluene | 0.00 | 65.09 | 99.74 | 99.68 | 0.05 | 0.00 |
|  | Acrylic acid | 67.99 | 32.18 | 0.16 | 0.09 | 0.92 | 99.91 |
|  | Acetic acid | 2.00 | 0.85 | 0.10 | 0.17 | 7.10 | 0.03 |
|  | Water | 29.99 | 1.82 | 0.00 | 0.06 | 91.93 | 0.00 |
|  | Heavies | 0.02 | 0.06 | 0.00 | 0.00 | 0.00 | 0.06 |

As shown in Table 3, in the case of Comparative Example 3, the concentration of acrylic acid included in the upper organic layer flow of the distillation column was confirmed to be 0.15 wt %, and the concentration of acrylic acid included in the upper aqueous layer flow was confirmed to be 1.27 wt %.

By comparison, as shown in Table 4, in the case of Example 1, by adjusting the tray open area ratio of perforated trays, the concentration of acrylic acid included in the upper organic layer flow and the concentration of acrylic acid included in the upper aqueous layer flow of the distillation column significantly decreased to 0.09 wt % and 0.92 wt %, respectively.

Further, in the case of Comparative Example 3, the temperature profile inside the distillation column significantly fluctuated. To the contrary, in the case of Example 1, the temperature profile inside the distillation column was stably maintained without fluctuation, and the ease of operation was significantly improved.

The invention claimed is:

1. An apparatus for continuous recovery of (meth)acrylic acid, comprising:
a (meth)acrylic acid absorption tower equipped with a mixed gas inlet to which mixed gas including (meth)acrylic acid, organic by-products, and vapor, which is produced by a synthesis reaction of (meth)acrylic acid, is fed, and a (meth)acrylic acid aqueous solution outlet from which a (meth)acrylic acid aqueous solution obtained by contact of the mixed gas with an absorption solvent including water is discharged;

a (meth)acrylic acid extraction column equipped with a (meth)acrylic acid aqueous solution inlet connected with the aqueous solution outlet of the absorption tower through an aqueous solution transfer line, to which a part of the (meth)acrylic acid aqueous solution is fed, an extract outlet from which the (meth)acrylic acid extract obtained by contact of the introduced (meth)acrylic acid aqueous solution with an extraction solvent is discharged, and a raffinate outlet from which the raffinate solution obtained by contact of the (meth)acrylic acid aqueous solution with an extraction solvent is discharged; and a distillation column equipped with a feed point that is connected with the (meth)acrylic acid aqueous solution outlet of the absorption tower through an aqueous solution transfer line, and is connected with the extract outlet of the extraction column through an extract transfer line, to which a feed containing the remainder of the (meth)acrylic acid aqueous solution and the extract solution is supplied, and a (meth)acrylic acid outlet from which (meth)acrylic acid obtained by distillation of the introduced feed is discharged, wherein the distillation column has a plurality of stages partitioned by perforated trays, and wherein, based on a feed point to which the feed is supplied, the distillation column comprises a rectifying section at an area above the feed point and a stripping section at an area below the feed point, wherein the tray open area of the perforated trays located at the rectifying section is lower than the tray open area of the perforated trays located at the stripping section.

2. The apparatus according to claim 1, wherein a ratio of the tray open area of the perforated trays located at the stripping section to the tray open area of the perforated trays located at the rectifying section of the distillation column is from 1:0.6 to 1:0.9.

3. The apparatus according to claim 1, wherein the perforated trays of the distillation column are dual-flow-type countercurrent trays.

4. The apparatus according to claim 1, wherein the feed point of the distillation column is any one point corresponding to 40 to 60% of total stages from the uppermost stage of the distillation column.

\* \* \* \* \*